United States Patent [19]

Ishizumi et al.

[11] Patent Number: 4,598,078

[45] Date of Patent: Jul. 1, 1986

[54] N-(SUBSTITUTED PIPERAZINYL) ALKYLBICYCLIC SUCCINIMIDE DERIVATIVES

[75] Inventors: Kikuo Ishizumi, Toyonaka; Fujio Antoku, Takarazuka; Yukio Asami, Kitamoto, all of Japan

[73] Assignee: Sumitomo Chemical Company, Limited, Osaka, Japan

[21] Appl. No.: 543,496

[22] Filed: Oct. 19, 1983

[30] Foreign Application Priority Data

Oct. 21, 1982 [JP] Japan .................. 57-185649

[51] Int. Cl.[4] ................. C07D 403/04; A61K 31/495
[52] U.S. Cl. .................. 514/252; 544/295; 544/360; 544/373; 514/218; 514/253; 260/245.7
[58] Field of Search ............ 424/244, 250, 251; 544/295, 373, 360

[56] References Cited

U.S. PATENT DOCUMENTS

| | | | |
|---|---|---|---|
| 2,343,198 | 2/1944 | Moore | 548/477 |
| 2,672,460 | 3/1954 | Conroy | 548/479 |
| 2,904,548 | 9/1959 | Rice et al. | 544/373 |
| 3,084,167 | 4/1963 | Rice | 544/373 |
| 3,198,798 | 8/1965 | Zenitz et al. | 544/373 |
| 3,362,956 | 1/1968 | Archer | 424/250 |
| 3,398,151 | 8/1968 | Wu | 424/250 |
| 3,472,855 | 10/1969 | Archer | 424/250 |
| 3,541,098 | 11/1970 | Mennear | 544/373 |
| 3,579,524 | 5/1971 | Van Dyke, Jr. | 544/373 |
| 3,717,634 | 2/1973 | Wu et al. | 424/250 |
| 3,850,992 | 11/1974 | Baum et al. | 424/340 |
| 3,907,801 | 9/1975 | Wu et al. | 424/250 |
| 3,917,636 | 11/1975 | Cusie et al. | 424/273 R |
| 3,976,776 | 8/1976 | Wu et al. | 514/255 |
| 4,182,763 | 1/1980 | Casten et al. | 424/251 |
| 4,261,990 | 4/1981 | Bowman | 424/267 |
| 4,507,303 | 3/1985 | Ishizumi et al. | 514/255 |
| 4,543,355 | 9/1985 | Ishizumi et al. | 514/253 |

FOREIGN PATENT DOCUMENTS

| | | | |
|---|---|---|---|
| 109562 | 5/1984 | European Pat. Off. | 544/295 |
| 2154520 | 9/1972 | France | 544/373 |
| 2101590 | 1/1983 | United Kingdom | 544/373 |

OTHER PUBLICATIONS

Korgaonkar, U. et al., Chem. Abst. 101: 23432k, (1984).
Zagidullin, R. N., Chemical Abstracts, 81:3881w, (1974).
Zagidullin, R. N., Chemical Abstracts, 81:3882x, (1974).
Journal of Medicinal Chemistry, vol. 15, No. 5 (1972), pp. 477-479.

Primary Examiner—George F. Lesmes
Assistant Examiner—S. A. Gibson
Attorney, Agent, or Firm—Birch, Stewart, Kolasch & Birch

[57] ABSTRACT

A succinimide derivative of the formula:

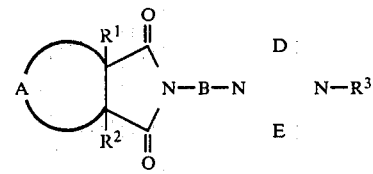

wherein A is straight or branched $C_2$–$C_6$ alkylene or alkenylene, B is straight or branched $C_3$–$C_5$ alkylene, D is straight or branched $C_2$–$C_3$ alkylene, E is straight or branched $C_2$–$C_3$ alkylene, $R^1$ and $R^2$ are each hydrogen or $C_1$–$C_4$ alkyl, or they may form a single bond and $R^3$ is a phenyl group optionally substituted with $C_1$–$C_4$ alkyl, $C_1$–$C_4$ alkoxy, halogen and/or trifluoromethyl, a 2-pyridyl group optionally substituted with halogen, a 2-pyrimidyl group optionally substituted with halogen, a group of the formula:

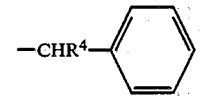

(in which $R^4$ is hydrogen or phenyl), a group of the formula: CO—$R^5$ (in which $R^5$ is adamantyl or furyl) or hydroxy ($C_2$–$C_4$) alkyl, and an acid addition salt thereof, which are useful as anti-anxiety drugs and/or anti-allergic drugs.

18 Claims, No Drawings

N-(SUBSTITUTED PIPERAZINYL) ALKYLBICYCLIC SUCCINIMIDE DERIVATIVES

The present invention relates to novel succinimide derivatives and their production. More particularly, it relates to novel succinimide derivatives having an aminoalkyl group at the N-position and their acid addition salts, and their production.

The succinimide derivatives of this invention can be represented by the formula:

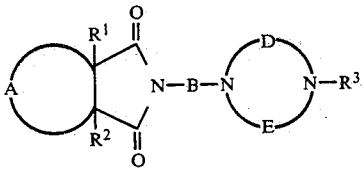
(I)

wherein A is straight or branched $C_2$–$C_6$ alkylene or alkenylene, B is straight or branched $C_3$–$C_5$ alkylene, D is straight or branched $C_2$–$C_3$ alkylene, E is straight or branched $C_2$–$C_3$ alkylene, $R^1$ and $R^2$ are each hydrogen or $C_1$–$C_4$ alkyl, or they may form a single bond and $R^3$ is a phenyl group optionally substituted with $C_1$–$C_4$ alkyl, $C_1$–$C_4$ alkoxy, halogen and/or trifluoromethyl, a 2-pyridyl group optionally substituted with halogen, a 2-pyrimidyl group optionally substituted with halogen, a group of the formula:

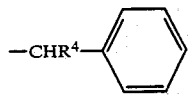

(in which $R^4$ is hydrogen or phenyl), a group of the formula: CO—$R^5$ (in which $R^5$ is adamantyl or furyl) or hydroxy($C_2$–$C_4$)alkyl.

In the above significances, the term "straight or branched $C_2$–$C_6$ alkylene" is intended to mean ethylene, trimethylene, tetramethylene, 2-methyltetramethylene, 1,4-dimethyltetramethylene, 2,3-dimethyltetramethylene, pentamethylene, hexamethylene, etc. The term "straight or branched $C_2$–$C_6$ alkenylene" means propenylene, 2-butenylene, 2-methyl-2-butenylene, 1,4-dimethyl-2-butenylene, 2,3-di- methyl-2-butenylene, pentenylene, hexenylene, etc. The term "straight or branched $C_3$–$C_5$ alkylene" includes trimethylene, tetramethylene, methyltetramethylene, pentamethylene, etc. The term "straight or branched $C_2$–$C_3$ alkylene" includes ethylene, methylethylene, trimethylene, etc. The term "$C_1$–$C_4$ alkyl" includes methyl, ethyl, propyl, butyl, etc. The term "$C_1$–$C_4$ alkoxy" includes methoxy, ethoxy, propoxy, butoxy, etc. The term "halogen" includes fluorine, chlorine or bromine. Examples of the term "hydroxy($C_2$–$C_4$)alkyl" are 2-hydroxyethyl, 3-hydroxypropyl, etc.

Preferable compounds in the succinimide derivatives (I) are those wherein A is tetramethylene, 2-methyltetramethylene, 1,4-dimethyltetramethylene, 2,3-dimethyltetramethylene, 2-butenylene, 2-methyl-2-butenylene, 1,4-dimethyl-2-butenylene, 2,3-dimethyl-2-butenylene, B is trimethylene, tetramethylene, pentamethylene, D and E are each ethylene, Rhu 1 and $R^2$ are each hydrogen, or they may form a single bond, and $R^3$ is a phenyl group optionally substituted with methyl, methoxy, halogen or trifluoromethyl, a 2-pyridyl group optionally substituted with halogen, a 2-pyrimidyl group optionally substituted with halogen or a benzyl group.

The succinimide derivatives (I) can form salts with acids such as inorgnanic acids (e.g. hydrochloric acid, hydrobromic acid, sulfuric acid, phosphoric acid) or organic acids (e.g. acetic acid, butyric acid, propionic acid, tartaric acid, citric acid, maleic acid, fumaric acid, methanesulfonic acid).

The succinimide derivatives (I) and their acid addition salts exhibit advantageous pharmaceutical properties such as anti-anxious activity and anti-allergic activity. They are thus useful for treatment of mammals in an anxious or allergic state.

The succinimide derivatives (I) can be prepared, for instance, by the processes as shown in the following scheme:

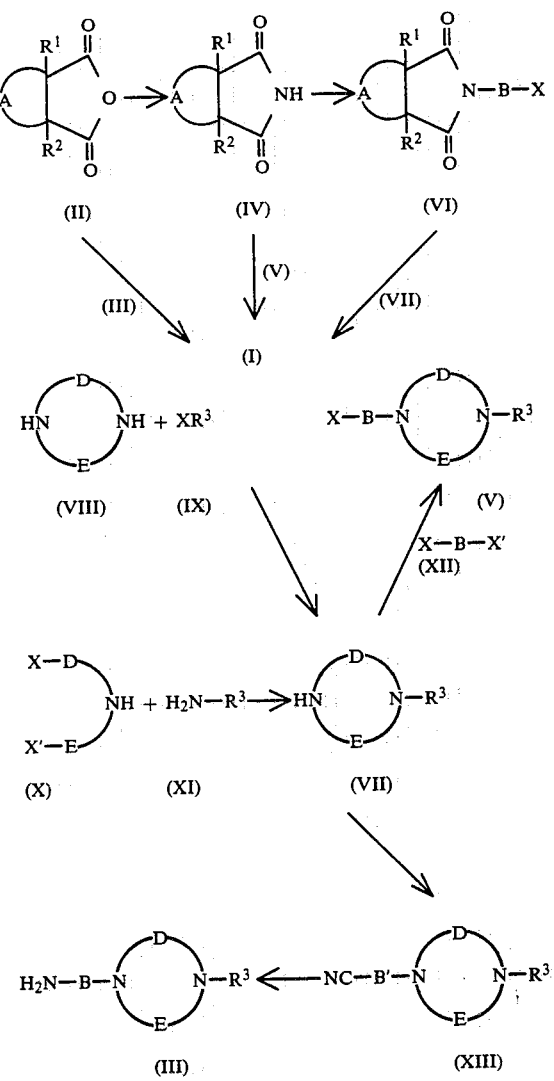

wherein A, B, D, E, $R^1$, $R^2$ and $R^3$ are each as defined above, X and X' are, the same or different, each a leaving group such as halogen (e.g. chlorine, bromine, iodine) or sulfonyloxy, especially alkanesulfonyloxy (e.g. methanesulfonyloxy) or arylsulfonyloxy (e.g. p-toluenesulfonyloxy) and B' is straight or branched $C_2$–$C_4$ alkylene.

The conversions in the above scheme will be hereinafter explained in detail.

Route A

The succinimide derivative (I) is prepared by reacting the acid anhydride (II) with the reagent (III), preferably in an inert organic solvent (e.g. pyridine, n-butanol, benzene, toluene, xylene) while refluxing.

Route B

The succinimide derivative (I) is prepared by reacting the imide (IV) with the reagent (V), preferably in an organic solvent (e.g. benzene, toluene, xylene, dimethylformamide, acetonitrile, n-butanol) in the existence of an acid binding agent at room temperature or while heating. The acid binding agent may be chosen from alkali metal or alkaline earth metal carbonates, bicarbonates and hydrides (e.g. potassium carbonate, sodium bicarbonate, sodium hydride), organic tertiary amines (e.g. triethylamine, pyridine), etc.

Route C

The succinimide derivative (I) is prepared by reacting the substituted imine (VI) with the reagent (VII), preferably in an organic solvent (e.g. benzene, toluene, xylene, dimethylformamide, acetonitrile, n-butanol) in the existence of an acid binding agent at room temperature or while heating. Examples of the acid binding agent are alkali metal or alkaline earth metal carbonates, bicarbonates and hydrides (e.g. potassium carbonate, sodium bicarbonate, sodium hydroxide), organic tertiary amines (e.g. triethylamine, pyridine), etc.

The starting compounds (II), (III), (IV), (V), (VI) and (VII) used in the above reactions are known or can be derived from known compounds as shown in the foregoing scheme.

The succinimide derivative (I) as obtained may be isolated from the reaction mixture in a per se conventional manner (e.g. distillation, crystallization, chromatography). Since the succinimide derivative (I) has basic nitrogen atoms and can form a salt with any acid, it is advantageously possible to make purification through a salt form.

Some typical examples of the succinimide derivative (I) are listed below:

N-[4-{4-(2-Pyrimidinyl)-1-piperazinyl}butyl]cyclobutane-1,2-dicarboximide;
N-[3-{4-(2-Pyrimidinyl)-1-piperazinyl}propyl]cyclobutane-1,2-dicarboximide;
N-[4-{4-(2-Pyrimidinyl)-1-piperazinyl}butyl]-4-cyclohexene-1,2-dicarboximide;
N-[3-{4-(2-Pyrimidinyl)-1-piperazinyl}propyl]-4 cyclohexene-1,2-dicarboximide;
N-[5-}4-(2-Pyrimidinyl)-1-piperazinyl}pentyl]-cyclohexane-1,2-dicarboximide;
N-[4-{4-(2-pyrimidinyl)-1-piperazinyl}butyl]-cyclohexane-1,2-dicarboximide;
N-[3-{4-(2-Pyrimidinyl)-1-piperazinyl}propyl]-cyclohexane-1,2-dicarboximide;
N-[4-{4-(5-Fluoro-2-pyrimidinyl)-1-piperazinyl}butyl]-cyclohexane-1,2-dicarboximide;
N-[3-{4-(5-Fluoro-2-pyrimidinyl)-1-piperazinyl}-propyl]cyclohexane-1,2-dicarboximide;
N-[4-{4-(2-Pyridyl)-1-piperazinyl}butyl]cyclo-hexane-1,2-dicarboximide;
N-[3-{4-(2-Pyridyl)-1-piperazinyl}propyl]cyclohexane-1,2-dicarboximide;
N-[3-{4-(3-Chloro-2-Pyridyl)-1-piperazinyl}propyl]cyclohexane-1,2-dicarboximide;
N-[3-{4-(3-Chloro-2-pyridyl)-1-piperazinyl}propyl]-cyclohexane-1,2-dicarboximide;
N-[4-{4-(5-Chloro-2-pyridyl)-1-piperazinyl}butyl]-cyclohexane-1,2-dicarboximide;
N-[4-(4-Phenyl-1-piperazinyl)butyl]cyclohexane-1,2-dicarboximide;
N-[3-(4-Phenyl-1-piperazinyl)propyl]cyclohexane-1,2-dicarboximide;
N-[4-{4-(2-Methylphenyl)-1-piperazinyl}butyl]- cyclohexane-1,2-dicarboximide;
N-[4-{4-(2-Methoxyphenyl)-1-piperazinyl}butyl]- cyclohexane-1,2-dicarboximide;
N-[4-{4-(2-Chlorophenyl)-1-piperazinyl}butyl]- cyclohexane-1,2-dicarboximide;
N-[3-{4-(2-Chlorophenyl)-1-piperazinyl}propyl]-cyclohexane-1,2-dicarboximide;
N-[4-{4-(3-Chlorophenyl)-1-piperazinyl}butyl]-cyclohexane-1,2-dicarboximide;
N-[3-{4-(3-Chlorophenyl)-1-piperazinyl}propyl]cyclohexane-1,2-dicarboximide;
N-[4-{4-(3-Trifluoromethylphenyl)-1-piperazinyl}-butyl]cyclohexane-1,2-dicarboximide;
N-[3-{4-(3-Trifluoromethylphenyl)-1-piperazinyl}-propyl]cyclohexane-1,2-dicarboximide;
N-[4-{4-(4-methylphenyl)-1-piperazinyl}butyl]- cyclohexane-1,2-dicarboximide;
N-[4-{4-(2-Pyrimidinyl)-1-homopiperazinyl}butyl]-cyclohexane-1,2-dicarboximide;
N-[4-{4-(2-Pyrimidinyl)-1-(2,5-dimethylpiperazinyl)}butyl]cyclohexane-1,2-dicarboximide;
N-[4-(4-Benzyl-1-piperazinyl)butyl]cyclohexane-1,2-dicarboximide;
N-[4-(4-Diphenylmethyl-1-piperazinyl)butyl]cyclohexane-1,2-dicarboximide;
N-[4-(4-Adamantoyl-1-piperazinyl)butyl]cyclohexane-1,2-dicarboximide;
N-[4-{4-(2-Furoyl)-1-piperazinylbutyl]cyclohexane -1,2-dicarboximide;
N-[4-{4-(2-Hydroxyethyl)-1-piperazinyl}butyl]- cyclohexane-1,2-dicarboximide;
N-[4-{4-(2-Pyrimidinyl)-1-piperazinyl}butyl]-1-cyclohexene-1,2-dicarboximide;
N-[3-4-(2-Pyrimidinyl)-1-piperazinyl}propyl]-1-cyclohexene-1,2-dicarboximide;
N-[4-{4-(2-Pyrimidinyl)-1-piperazinyl}butyl]-4-methyl-4-cyclohexene-1,2-dicarboximide;
N-[3-{4-(2-Pyrimidinyl)-1-piperazinyl}propyl]-4-methyl-4-cyclohexene-1,2-dicarboximide;
N-[4-{4-(2-Pyridyl)-1-piperazinyl}butyl]-4-methyl-4-cyclohexene-1,2-dicarboximide;
N-[4-{4-(2-Pyrimidinyl)-1-piperazinyl}butyl]-4-methyl-cyclohexane-1,2-dicarboximide;
N-[3-{4-(2-Pyrimidinyl)-1-piperazinyl}propyl]-4-methylcyclohexane-1,2-dicarboximide;
N-[4-{4-(5-Fluoro-2-pyrimidinyl)-1-piperazinyl}butyl]-4-methylcyclohexane-1,2-dicarboximide;
N-[4-{4-(2-Pyridyl)-1-piperazinyl}butyl]-4-methyl- cyclohexane-1,2-dicarboximide;
N-[4-{4-(2-Pyrimidinyl)-1-piperazinyl}butyl]-3,6-dimethyl-4-cyclohexene-1,2-dicarboximide;
N-[4-{4-(2-Pyrimidinyl)-1-piperazinyl}butyl]-3,6-dimethylcyclohexane-1,2-dicarboximide;
N-[4-{4-(2-Pyrimidinyl)-1-piperazinyl}butyl]-4,5-dimethyl-4-cyclohexene-1,2-dicarboximide;
N-[4-{4-(2-Pyrimidinyl)-1-piperazinyl}butyl]-4,5-dimethylcyclohexane-1,2-dicarboximide;

N-[4-4-(2-Pyrimidinyl)-1-piperazinyl}butyl]-1,2-dimethylcyclohexane-1,2-dicarboximide;
N-[3-{4-(2-Pyrimidinyl)-1-piperazinyl}propyl]-4,5-dimethylcyclohexane-1,2-dicarboximide, etc.

As stated above, the succinimide derivatives (I) and their acid addition salts exhibit an anti-anxious activity, which could be proved by the anti-conflict test as described in Geller and Seifter: Psychopharmacologia, 1, 482 (1960).

Hungry male rats (Kitayama) of Wistar strain which were previously trained to take feed by levering were negatively reinforced by receiving an electric shock on levering. As the result, the rats fall into conflict and stopped to levering. When an anti-anxiety substance was administered to the rats, the rats reopened the levering despite receiving the electric shock. Frequency of the levering under the electric shock was used for indication of the anti-conflict or anti-anxious activity of the test substance. The test substance was administered intraperitoneally to the rats. Tests were carried out while the activity of the substance was the maximum. The known anti-anxiety drug "Diazepam" was used for the control. A dose of 3 mg/kg (i.p.) of N-[4-{4-(2-pyrimidinyl)-1piperazinyl}butyl]cyclohexane-1,2-dicarboximide hydrochloride (Compound A) had an approximately equal anti-conflict or anti-anxiety activity to 1 mg/kg (i.p.) of Diazepam, and afforded no substantial influence on the general behavior.

Further, the compound (A) did not show any significant effect at a dose of 100 mg/kg (per os) on hexobarbital anesthesia which is an indication of depressing side effect such as sleepiness, while Diazepam reinforced the anesthesia significantly at a dose of 1 mg/kg (per os). It was proved from these results that the compound (A) is a selective antianxiety drug with less central nervous side effects.

The succinimide derivatives (I) and their acid addition salts also exhibit an anti-allergic activity, which can be demonstrated according to the process as described in Z. Ovary: Progr. Allergy, 5, 459 (1958). For instance, it was proved by the PCA test described therein that N-[4-(4-benzyl-1-piperadinyl)butyl]cyclohexane-1,2-dicarboximide hydrochloride (Compound B) of the invention has a significant anti-allergic activity.

For therapeutic administration, the compound (I) or the salt thereof may be used in the form of conventional pharmaceutical preparations suitable for oral administration, for example, tablet, capsule, syrup, suspension, etc., or those suitable for parenteral administration, for example, solution, emulsion, suspension, etc. for injection, or suppository for rectal administration with or without a suitable carrier such as filler, binder or stabilizer. In case of the injection, there may be included in the above preparations pharmaceutically acceptable buffers, solubilizers, isotonizers, etc.

While the dosage of the compound (I) may vary from and also depend upon the degree of the infection, age and weight of patient and dosage forms, the active compound can be, in general, administered to adult in an amount between 1 mg and 500 mg, preferably 5 mg and 200 mg per day in single dose or divided doses.

The present invention will be further illustrated in detail by means of the following Reference Examples and Examples, which are not, however, intended to limit the scope of the invention.

REFERENCE EXAMPLE 1

A mixture of 2,3-dimethyl-1,3-butadiene (10 g; 0.122 mol), maleic anhydride (11.9 g; 0.122 mol) and benzene (30 ml) was stirred at room temperature for 10 hours. Precipitates were removed by filtration, and the filtrate was evaporated under reduced pressure to give 4,5-dimethyl-4-cyclohexene-1,2-dicarboxylic anhydride. M.P., 73–74° C.

REFERENCE EXAMPLE 2

A mixture of 4,5-dimethyl-4-cyclohexene-1,2-dicarboxylic anhydride (10 g; 0.0555 mol), platinum dioxide (150 mg) and tetrahydrofuran (100 ml) was hydrogenated at room temperature for 8 hours. Precipitates were removed by filtration, and the filtrate was evaporated under reduced pressure to give 4,5-dimethylcyclohexene-1,2-dicarboxylic anhydride. IR $\nu_{max}^{Film}$ (cm$^{-1}$): 1860, 1760.

In the same manner as in Reference Example 1 or 2, there were obtained the following compounds:
3,6-Dimethyl-4-cyclohexene-1,2-dicarboxylic anhydride, M.P., 43°–45° C.;
3,6-Dimethylcyclohexane-1,2-dicarboxylic anhydride, IR $\nu_{max}^{Film}$ (cm$^{-1}$): 1855, 1790.
1,2-Dimethyl-4-cyclohexene-1,2-dicarboxylic anhydride, M.P., 98°–99° C.;
1,2-Dimethylcyclohexane-1,2-dicarboxylic anhydride, IR $\nu_{max}^{Film}$ (cm$^{-1}$): 1845, 1825, 1780.

REFERENCE EXAMPLE 3

A mixture of cis- 4-tetrahydrophthalimide (20 g; 0.132 mol), 50% water-containing 5% palladium-carbon (2 g) and tetrahydrofuran (200 ml) was halogenated at room temperature for 8 hours. Precipitates were removed by filtration, and the filtrate was evaporated under reduced pressure to give cyclohexane-1,2-dicarboximide. IR $\nu_{max}^{Film}$ (cm$^{-1}$): 1760, 1720, 1700.

REFERENCE EXAMPLE 4

A mixture of 1,2-cyclohexanedicarboxylic anhydride (3 g; 19.5 mmol) and 29% aqueous ammonia (3.4 g) was heated and kept at an inner temperature of 180°–190° C. for 2 hours to give cyclohexane-1,2-dicarboximide. M.P. 132°–136° C.

REFERENCE EXAMPLE 5

To a solution of cyclohexane-1,2-dicarboximide (10 g; 65.3 mmol) in anhydrous dimethylformamide (50 ml), there was added 60% sodium hydride (2.6 g; 68.5 mmol) under nitrogen at room temperature, and the resultant mixture was stirred at the same temperature for 3 hours. Tetramethylene bromide (70.5 g; 0.327 mol) was added thereto, and the mixture was stirred for 3 hours. After completion of the reaction, the resultant mixture was poured into water and extracted with ethyl acetate. The organic layer was washed with water twice and with a saturated sodium chloride solution. The organic layer was dried over anhydrous magnesium sulfate, and the solvent and excessive tetramethylene bromide were removed by evaporation to give N-(4-bromobutyl)cyclohexane-1,2-dicarboximide. IR $\nu_{max}^{Film}$ (cm$^{-1}$): 1770, 1700.

In the same manner as in Reference Example 5, there was obtained the following compound:
N-(3-Chloropropyl)-4-cyclohexane-1,2-dicarboximide, IR $\nu_{max}^{Film}$ (cm$^{-1}$): 1770, 1700.

REFERENCE EXAMPLE 6

A mixture of di(2-bromoethyl)amine hydrobromide (15.6 g; 0.05 mol), 3-aminobenzotrifluoride (24.2 g; 0.15 mol) and methylethylketone (50 ml) was heated under reflux for 4 hours, and the resultant mixture was neutralized with a dilute sodium hydroxide solution and extracted with ether. The ethereal layer was washed with a saturated sodium chloride solution and dried over anhydrous magnesium sulfate. The solvent was removed under reduced pressure, and the residue was distilled to give N-(α, α, α-trifluorom-tolyl)piperazine. B.P., 130°–140° C./0.3 mmHg.

REFERENCE EXAMPLE 7

To a solution of anhydrous piperazine (95 g; 1 mol) in ethanol (475 ml), there was added 2-chloropyrimidine (22.9 g; 0.2 mol), and the resultant mixture was stirred at room temperature for 3 hours. After completion of the reaction, a 5% aqueous sodium hydroxide solution was added, followed by extraction with chloroform. The chloroform layer was washed thrice with water and dried over anhydrous magnesium sulfate. The solvent was removed under reduced pressure, and the residue was distilled to give 1-(2-pyrimidinyl)piperazine. B.P., 131°–132° C./1.5 mmHg.

REFERENCE EXAMPLE 8

A mixture of 1-(2-pyrimidinyl)piperazine (2 g; 12.2 mmol), acetone (2 ml), 1-bromo-3-chloropropane (2.5 g; 15.9 mmol) and a 25% aqueous sodium hydroxide solution (1.9 ml) was stirred at room temperature for 6 hours. After completion of the reaction, the resultant mixture was poured into water and extracted with ethyl acetate. The organic layer was washed with a saturated sodium chloride solution and dried over anhydrous magnesium sulfate. The solvent was removed under reduced pressure to give 1-(3-chloropropyl)-4-(2-pyrimidinyl)piperazine. IR $\nu_{max}^{Film}$ (cm$^{-1}$): 1595, 1550, 1500.

In the same manner as in Reference Example 8, there were obtained the following compounds:
1-(3-Chloropropyl)-4-(2-pyridyl)piperazine, IR $\nu_{max}^{Film}$ (cm$^{-1}$): 1590, 1480.
b 1-(3-Chloropropyl)-4-phenylpiperazine, IR $\nu_{max}^{Film}$ (cm$^{-1}$): 1600, 1500.

REFERENCE EXAMPLE 9

A mixture of 4-chlorobutyronitrile (3.3 g; 0.032 mol), 1-(2-pyrimidinyl)piperazine (3.3 g; 0.032 mol), sodium carbonate (6.4 g; 0.0608 mol) and n-butanol (50 ml) was heated under reflux for 19 hours. After completion of the reaction, the resultant mixture was poured into water and extracted with ethyl acetate. The organic layer was washed with a saturated sodium chloride solution and dried over anhydrous magnesium sulfate. The solvent was removed under reduced pressure, and the residue was purified by silica gel chromatography to give 1-(3-cyanopropyl)-4-(2-pyrimidinyl)-piperazine. M.P., 56°–57° C.

REFERENCE EXAMPLE 10

To a cold mixture of lithium aluminum hydride (2.0 g; 5.26 mmol) and anhydrous ether (240 ml) kept at a temperature of −54° C., there was dropwise added a solution of 1-(3-cyanopropyl)-4-(2-pyrimidinyl)piperazine (8 g; 3.46 mmol) in anhydrous ether (80 ml), and the resultant mixture was kept at the same temperature as above for 1.5 hours, followed by dropwise addition of water (2 ml), a 15% aqueous potassium hydroxide solution (2 ml) and water (6 ml) in order. The reaction mixture was stirred at room temperature for 2 hours, subjected to filtration with celite and washed with chloroform. The filtrate was concentrated under reduced pressure, and the residue was purified by silica gel chromatography to give 1-(4-aminobutyl)-4-(2-pyrimidinyl)-piperazine. IR $\nu_{max}^{Film}$ (cm$^{-1}$): 3100–3600, 1580, 1540.

EXAMPLE 1

A mixture of cis-4-cyclohexene-1,2-dicarboxylic anhydride (633 mg; 4.25 mmol), 1-(4-aminobutyl)-4-(2-pyrimidinyl)piperazine (1 g; 4.25 mmol) and n-butanol (10 ml) was heated under reflux for 6 hours. The solvent was removed under reduced pressure, and the residue was purified by silica gel chromatography to give an oily substance. The oily substance was treated with a mixture of 3% hydrogen chloride in isopropanol, and the precipitate was recrystallized from isopropanol to give N-[4-{4-(2-pyrimidinyl)-1-piperazinyl}butyl]-4-cyclohexene-1,2-dicarboximide hydrochloride. M.P., 177°–179° C.

EXAMPLE 2

To a solution of cyclohexane-1,2-dicarboximide (6.50 g) in anhydrous dimethylformamide (65 ml), a 60% mineral oil suspension of sodium hydride (1.60 g) was added at room temperature while stirring, and the resultant mixture was continuously stirred for 30 minutes. A solution of 3-[4-(2-pyrimidinyl)piperazinyl]propyl chloride (11.30 g) in anhydrous dimethylformamide (30 ml) was dropwise added thereto, and the resultant mixture was stirred at room temperature for 4.5 hours. The solvent was removed under reduced pressure, and the residue was purified by chromatography to give an oily substance, which was then treated with hydrogen chloride to give N-[3-{4-(2-pyrimidinyl)-1-piperazinyl}propyl]cyclohexane-1,2-dicarboximide hydrochloride. M.P., 180°–182° C.

EXAMPLE 3

A mixture of N-(4-bromobutyl)cyclohexane-1,2-dicarboximide (10.00 g), 1-(2-pyrimidyl)piperazine (4.75 g), anhydrous potassium carbonate powder (8.00 g) and anhydrous dimethylformamide (100 ml) was stirred at 100°–110° C. for 9 hours. The solvent was removed from the reaction mixture under reduced pressure, and the residue was purified by chromatography to give an oily substance, which was then treated with hydrogen chloride to give N-[4-{4-(2-pyrimidinyl)-1-piperazinyl}butyl]cyclohexane-1,2-dicarboximide hydrochloride. M.P., 168°–169° C.

In the same manner as in any of Examples 1 to 3, there were obtained the following compounds:
N-[4-{4-(2-Pyrimidinyl)-1-piperazinyl}butyl]-cyclobutane-1,2-dicarboximide hydrochloride, M.P., 212°–215° C. (decomp.);
N-[4-{4-(2-Pyrimidinyl)-1-piperazinyl}butyl]-4-cyclohexene-1,2-dicarboximide hydrochloride, M.P. 177°–179° C.;
N-[5-{4-(2-Pyrimidinyl)-1-piperazinyl}pentyl]-cyclohexane-1,2-dicarboximide hydrochloride, M.P., 180°–182° C.;
N-[4-{4-(2-Pyrimidinyl)-1-piperazinyl}butyl]-cyclohexane-1,2-dicarboximide hydrochloride, M.P., 179°–181° C.;

N-[3-{4-(2-Pyrimidinyl)-1-piperazinyl}propyl]-cyclohexane-1,2-dicarboximide hydrochloride, M.P. 180°–182° C.;

N-[4-{4-(5-Fluoro-2-pyrimidinyl)-1-piperazinyl}butyl]-cyclohexane-1,2-dicarboximide, M.P., 225°–226.5° C.;

N-[4-{4-(2-Pyridyl)-1-piperazinyl}butyl]cyclohexane-1,2-dicarboximide hydrochloride, M.P., 135°–137° C.;

N-[4-{4-(3-Chloro-2-pyridyl)-1-piperazinyl}butyl]-cyclohexane-1,2-dicarboximide, M.P., 66°–68° C.;

N-[4-{4-(5-Chloro-2-pyridyl)-1-piperazinyl}butyl]-cyclohexane-1,2-dicarboximide, M.P. 102°–103° C.;

N-[4-(4-Phenyl-1-piperazinyl)butyl]cyclohexane-1,2-dicarboximide hydrochloride, M.P., 229°–230° C.;

N-[4-{4-(2-Methylphenyl)-1-piperazinyl}butyl]-cyclohexane-1,2-dicarboximide hydrochloride, M.P., 203° C. decomp.);

N-[4-{4-(2-Methoxyphenyl)-1-piperazinyl}butyl]-cyclohexane-1,2-dicarboximide hydrochloride, M.P., 197°–200° C.;

N-[4-{4-(2-Chlorophenyl)-1-piperazinyl}butyl]-cyclohexane-1,2-dicarboximide hydrochloride, M.P., 178°–181° C.;

N-[4-{4-(3-Chlorophenyl)-1-piperazinyl}butyl]-cyclohexane-1,2-dicarboximide hydrochloride, M.P., 187°–192° C.;

N-[4-{4-(3-Trifluoromethylphenyl)-1-piperazinyl}butyl]cyclohexane-1,2-dicarboximide hydrochloride, M.P. 178°–180° C.;

N-[4-{4-(4-Methylphenyl)-1-piperazinyl}butyl]-cyclohexane-1,2-dicarboximide hydrochloride, M.P., 234°–235° C.;

N-[4-{4-(2-Pyrimidinyl)-1-homopiperazinyl}butyl]- cyclohexane-1,2-dicarboximide, IR $\nu_{max}^{Film}$ (cm$^{-1}$) : 1760, 1695, 1580;

N-[4-{4-(2-Pyrimidinyl)-1-(2,5-dimethylpiperazinyl} butyl]cyclohexane-1,2-dicarboximide, IR $\nu_{max}^{Film}$ (cm$^{-1}$): 1770, 1700, 1585;

N-[4-(4-Benzyl-1-piperazinyl)butyl]cyclohexane-1,2-dicarboximide hydrochloride, M.P., 253°–255° C.;

N-[4-(4-Diphenylmethyl-1-piperazinyl)butyl]cyclohexane 1,2-dicarboximide hydrochloride, M.P. 223°–225° C.;

N-[4-(4-Adamantoyl-1-piperazinyl)butyl]cyclohexane-1,2-dicarboximide hydrochloride, M.P. 270°–272° C.;

N-[4-{4-(2-Furoyl)-1-piperazinyl}butyl]cyclohexane-1,2-dicarboximide hydrochloride, M.P. 199°–200° C.;

N-[4-{4-(2-Hydroxyethyl)-1-piperazinyl}butyl]-cyclohexane-1,2-dicarboximide hydrochloride, M.P., 250°–252° C.;

N-[4-{4-(2-Pyrimidinyl)-1-piperazinyl}butyl]-1-cyclohexene-1,2-dicarboximide hydrochloride, M.P., 194°–196° C.;

N-[4-{4-(2-Pyrimidinyl)-1-piperazinyl}butyl]-4-methyl-4-cyclohexene-1,2-dicarboximide hydrochloride, M.P., 164°–165.5° C.;

N-[4-{4-(2-Pyridyl)-1-piperazinyl}butyl]-4-methyl-4-cyclohexene-1,2-dicarboximide hydrochloride, M.P. 122° C. (decomp.);

N-[4-{4-(2-Pyrimidinyl)-1-piperazinyl}butyl]-4-methylcyclohexane-1,2-dicarboximide hydrochloride, M.P., 156°–158° C.;

N-[4-{4-(2-Pyridyl)-1-piperazinyl}butyl]-4-methylcyclohexane-1,2-dicarboximide hydrochloride, M.P., 125° C. (decomp.);

N-[4-{4-(2-Pyrimidinyl)-1-piperazinyl}butyl]-3,6-dimethylcyclohexane-1,2-dicarboximide hydrochloride, M.P., 137° C. (decomp.);

N-[4-{4-(2-Pyrimidinyl)-1-piperazinyl}butyl]-4,5-dimethyl-4-cyclohexene-1,2-dicarboximide hydrochloride, M.P., 209°–211° C.;

N-[4-{4-(2-Pyrimidinyl)-1-piperazinyl}butyl]-4,5-dimethylcyclohexane-1,2-dicarboximide hydrochloride, M.P., 225°–227° C.;

N-[4-{4-(2-Pyrimidinyl)-1-piperazinyl}butyl]-1,2-dimethylcyclohexane-1,2-dicarboximide hydrochloride, M.P., 208°–210° C. (decomp.); etc.

What is claimed is:

1. A succinimide compound of the formula:

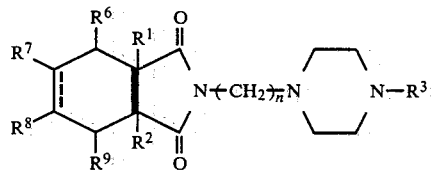

wherein $R^1$ and $R^2$ are each hydrogen or $C_1$–$C_4$ alkyl, or they may form a single bond; $R^3$ is a phenyl group, a phenyl group mono-substituted with $C_1$–$C_4$ alkyl $C_1$–$C_4$ alkoxy, halogen or trifluoromethyl, a 2-pyridyl group, a 2-pyridyl group mono-substitued with halogen, a 2-pyrimidyl group, a 2-pyrimidyl group mono-substituted with halogen, a group of the formula:

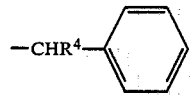

(in which $R^4$ is hydrogen or phenyl), a group of the formula: CO—$R^5$ (in which $R^5$ is adamantyl or furyl) or hydroxy($C_2$–$C_4$)alkyl; $R^6$, $R^7$, $R^8$ and $R^9$ are each hydrogen or methyl; n is an integer of 3 to 5; a full line accompanying a broken line (- - - - - -) indicates a single or double bond or an acid addition salt thereof.

2. The succinimide derivative as claimed in claim 1, which is a compound of the formula:

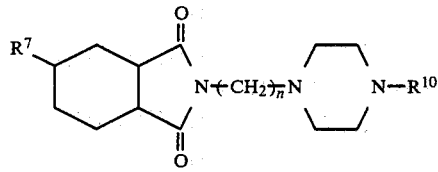

wherein n is an integer of 3 to 5, $R^7$ is hydrogen or methyl and $R^{10}$ is a phenyl group, a phenyl group mono-substituted with $C_1$–$C_4$ alkyl, $C_1$–$C_4$ alkoxy, halogen or trifluoromethyl, a 2-pyridiyl group, a 2-pyridiyl group mono-substituted with halogen, a pyrimidyl group, or a 2-pyrimidyl group mono-substituted with halogen, or an acid addition salt thereof.

3. The compound as claimed in claim 1, which is N-[4-{4-(2-pyrimidinyl)-1-piperazinyl}butyl]-4-cyclohexene-1,2dicarboximide or an acid addition salt thereof.

4. The compound as claimed in claim 1, which is N-[3-{4-(2-pyrimidinyl)-1-piperazinyl}propyl]cyclohexane-1,2-dicarboximide or an acid addition salt thereof.

5. The compound as claimed in claim 1, which is N-[4-{4-(2-pyrimidinyl)-1-piperazinyl}butyl]cyclohexane-1,2-dicarboximide or an acid addition salt thereof.

6. The compound as claimed in claim 1, wherein $R^1$ and $R^2$ are each hydrogen.

7. The compound as claimed in claim 1, wherein at least one of $R^1$ or $R^2$ is a $C_1$-$C_4$ alkyl group.

8. The compound as claimed in claim 1, wherein $R^3$ is a phenyl group or a phenyl group mono-substituted with $C_1$-$C_4$ alkyl, $C_1$-$C_4$ alkoxy, halogen or trifluoromethyl.

9. The compound as claimed in claim 1, wherein $R^3$ is a 2-pyridyl group or a 2-pyridyl group mono-substituted with halogen.

10. The compound as claimed in claim 1, wherein $R^3$ is a 2-pyrimidyl group or a 2-pyrimidyl group mono-substituted with halogen.

11. A pharmaceutical composition which comprises as an active ingredient a pharmaceutically effective amount of at least one of the compounds claimed in claim 1 and at least one pharmaceutically acceptable inert carrier or diluent.

12. The composition as recited in claim 11, which is in the form of a tablet, capsule, syrup or suspension.

13. The composition as recited in claim 11, which is in the form of an emulsion, solution or suspension.

14. The composition as recited in claim 11, which is in the form of a suppository.

15. A method for reducing anxiety or allergic activity which comprises administering an effective anti-anxious or antiallergic amount of the compound as recited in claim 1 to a mammal.

16. The method as recited in claim 15, wherein 1 to 500 mg of the succinimide is administered daily in a single dose or divided doses.

17. A method for reducing anxiety or allergic activity which comprises orally administering an effective anti-anxious or anti-allergic amount of the composition as recited in claim 12.

18. A method for reducing anxiety or allergic activity which comprises parenterally administering an effective anti-anxious or anti-allergic amount of the composition as recited in claim 13.

* * * * *